United States Patent [19]
Johnson et al.

[11] Patent Number: 4,932,633
[45] Date of Patent: Jun. 12, 1990

[54] HEMOSTASIS VALVE

[75] Inventors: Wade M. Johnson, Minneapolis; Edward A. Barlow, Bloomington; Gregory G. Brucker, Minneapolis, all of Minn.

[73] Assignee: Schneider-Shiley (U.S.A.) Inc., Plymouth, Minn.

[21] Appl. No.: 273,584

[22] Filed: Nov. 21, 1988

[51] Int. Cl.$^5$ ............................................ F16L 37/28
[52] U.S. Cl. .................... 251/149.1; 604/256; 604/905
[58] Field of Search .................... 604/256, 905; 251/149.1

[56] References Cited

U.S. PATENT DOCUMENTS

| | | | |
|---|---|---|---|
| 3,837,381 | 9/1974 | Arroyo | 251/149.1 |
| 4,000,739 | 1/1977 | Stevens | 128/568 |
| 4,430,081 | 2/1984 | Timmermans | 251/149.1 |
| 4,436,519 | 3/1984 | O'Neill | 604/256 |
| 4,547,194 | 10/1985 | Moorehead | 604/905 |
| 4,626,245 | 12/1986 | Weinstein | 604/167 |

Primary Examiner—A. Michael Chambers
Attorney, Agent, or Firm—Haugen and Nikolai

[57] ABSTRACT

A hemostasis valve gasket for use in an introducer which is integrally formed from an elastomeric material so as to exhibit resiliency and which is designed to close about small diameter objects, such as a guide wire and about larger diameter objects such as a working catheter or guide catheter to prevent air or blood leakage. The gasket includes a proximal cylindrical member, a distal cylindrical member and a central member which is spaced in its center portion from the proximal and distal members by chambers or cavities. One of the proximal or distal cylindrical members has a bore of a relatively small diameter compared to that formed through the other and an angled slit is formed through the central member in general alignment with the bores formed through the outer proximal and distal cylindrical members.

11 Claims, 4 Drawing Sheets

HEMOSTASIS VALVE

BACKGROUND OF THE INVENTION

This invention relates to a hemostasis valve used in conjunction with a cannula to position and manipulate intravascular catheters of the type typically used in angiography or angioplasty procedures. Angiography is a well known and very valuable procedure used in the diagnosis of vascular and organ disease. Angioplasty has, in recent years, come into its own as a viable method for treating blockages in the coronary arteries. Both of these procedures involve inserting a catheter into one of the major arteries or veins and then advancing it into smaller branching vessels.

One prior art technique for inserting such catheters is known as the "cut down" method. This method involves surgically opening of vein or artery and inserting the catheter directly through the incision. This method is not preferred because it inevitably involves the loss of blood through the incision. This procedure also requires, in nearly all instances, venus ligation and arterial repair.

More recently, physicians have adopted an alternative procedure which includes placing a percutaneous sheath, called an introducer, into the blood vessel. A guide wire is then passed through the introducer and advanced up the artery or vein to the area to be studied or treated. Once the guide wire is in place, a catheter is inserted through the introducer and over the guide wire until the catheter working end reaches the treatment or study site.

A recognized problem with this latter technique is excess bleeding and the possibility of air embolisms, particularly during the insertion, removal or change of catheters. To reduce the possibility of excess loss of blood and/or the development of air embolisms, many attempts have been made to develop a suitable hemostasis valve or gasket for use in conjunction with the introducer. U.S. Pat. No. 4,000,739, issued on Jan. 4, 1977 to Robert C. Stevens, discloses a gasket system which is intended to inhibit excess bleeding and prevent the development of emboli. This system involves the use of two disk like gaskets formed from an elastomeric material. The first gasket has a round hole through its center and the second gasket has Y-shaped slit through its center. When stacked face-to-face, these gaskets cooperate to close the passage about the catheter during insertion and during manipulation of the catheter. Following removal of the catheter, the Y-shaped slit closes to prevent blood air from flowing therethrough.

U.S. Pat. No. 4,436,519, issued on Mar. 13, 1984 to William J. O'Neil, discloses a dome-shaped hemostasis valve which is directed to these same problems. This valve has a body comprised of a central passage and a resilient dome-shaped diaphragm having a wall member with a single linear slit. A dome-shaped diaphragm is used because it will act in cooperation with the walls of central passage to resiliently urge the slit closed when no catheter is present therethrough.

Still another valve arrangement is disclosed in U.S. Pat. No. 4,626,245 to Weinstein. This patent discloses an elastomeric partition valve of one piece construction. The valve includes a first slit defined by one side of the partition valve and a second slit defined by the opposite side. Each slit has a location which creates two spaced apart points of intersection with the other slit. The Weinstein Patent further indicates that the first and second slit should both have a Y-shape.

While each of the designs discussed above have certain advantages, none of them are deemed to be fully satisfactory. For example, each permits a certain amount of blood leakage because they do not provide a sufficiently tight seal when only the guide wire is in place. This is particularly true for smaller diameter guide wires.

SUMMARY OF THE INVENTION

It is therefore an object of the present invention to provide a hemostasis valve for use with an introducer which will inhibit of eliminate flow of blood through the valve during insertion and manipulation of either a guide wire or a catheter during an angioplasty or angiography procedure. More specifically, it is the object of this invention to provide an improved valve having three separate members which cooperate to perform the leak proof valve function.

In general, the valve of the present invention is molded or otherwise formed from a suitable elastomeric material and has a proximal member, a center member and a distal member, all of which are cylindrical in shape. The proximal and distal members have approximately the same diameter which is smaller than the diameter of the central member. The "extra" diameter of the central section is present to form a flange by which the valve can be secured into an introducer body to form a tight seal between the valve's circumference and the inner wall of the introducer.

Both the proximal member and the distal member has a hole therethrough, the two holes being aligned with one another. The central member has an angled slit extending through its thickness dimension, the slit also being aligned with the holes of the proximal and distal members. The two holes and the slit are sized so that a relatively small diameter guide wire or a larger diameter catheter can be passed through them. An important feature of the present invention is the angular orientation of the slit. Preferably, the slit is cut at approximately 45° through the central member. Cutting the slit in this fashion promotes an improved seal around the guide wire and/or catheter. It also ensures a quick, tight seal of the valve when such penetrating objects are removed.

DETAILED DESCRIPTION OF THE INVENTION

Figure 3:
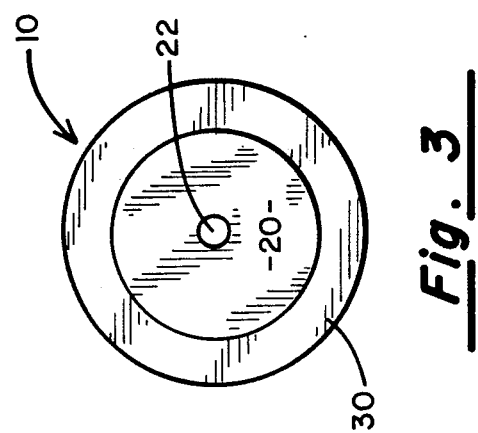
FIG. 3 is a plan view of the distal end of the valve of the present invention.
Figure 3A:
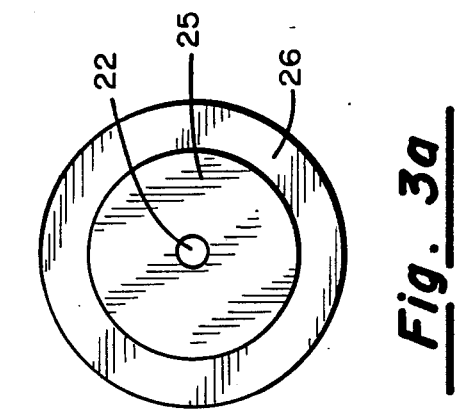
FIGS. 1A, 2A and 3A correspond to FIGS. 1, 2 and 3 respectively, but relate to an alternative embodiment of the present invention.
Figure 2:
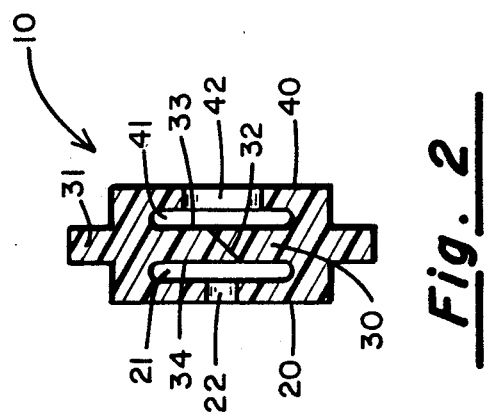
FIG. 2 is a cross-sectional view taken through line 2—2 of FIG. 1.
Figure 2A:
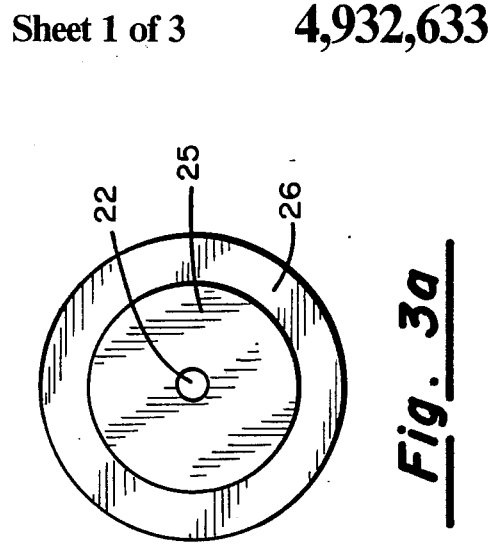
Figure 1:
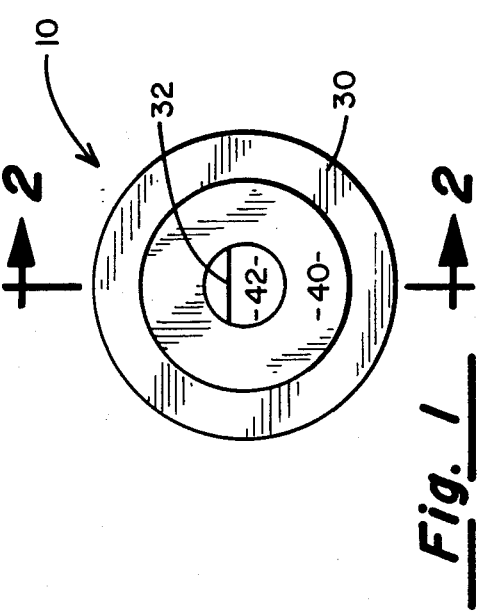
FIG. 1 is a plan view of the proximal end of the valve of the present invention.
Figure 1A:
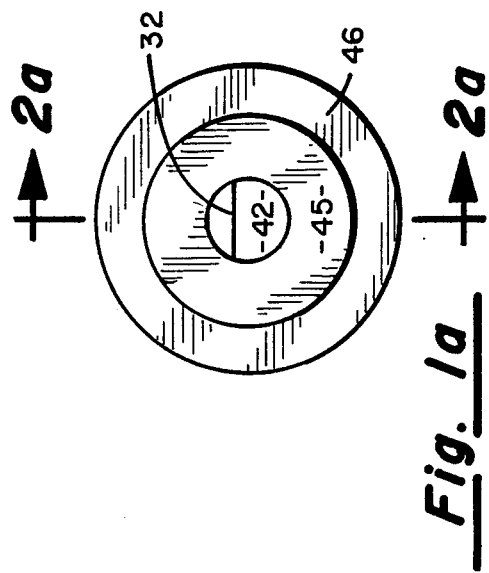
Figure 4:
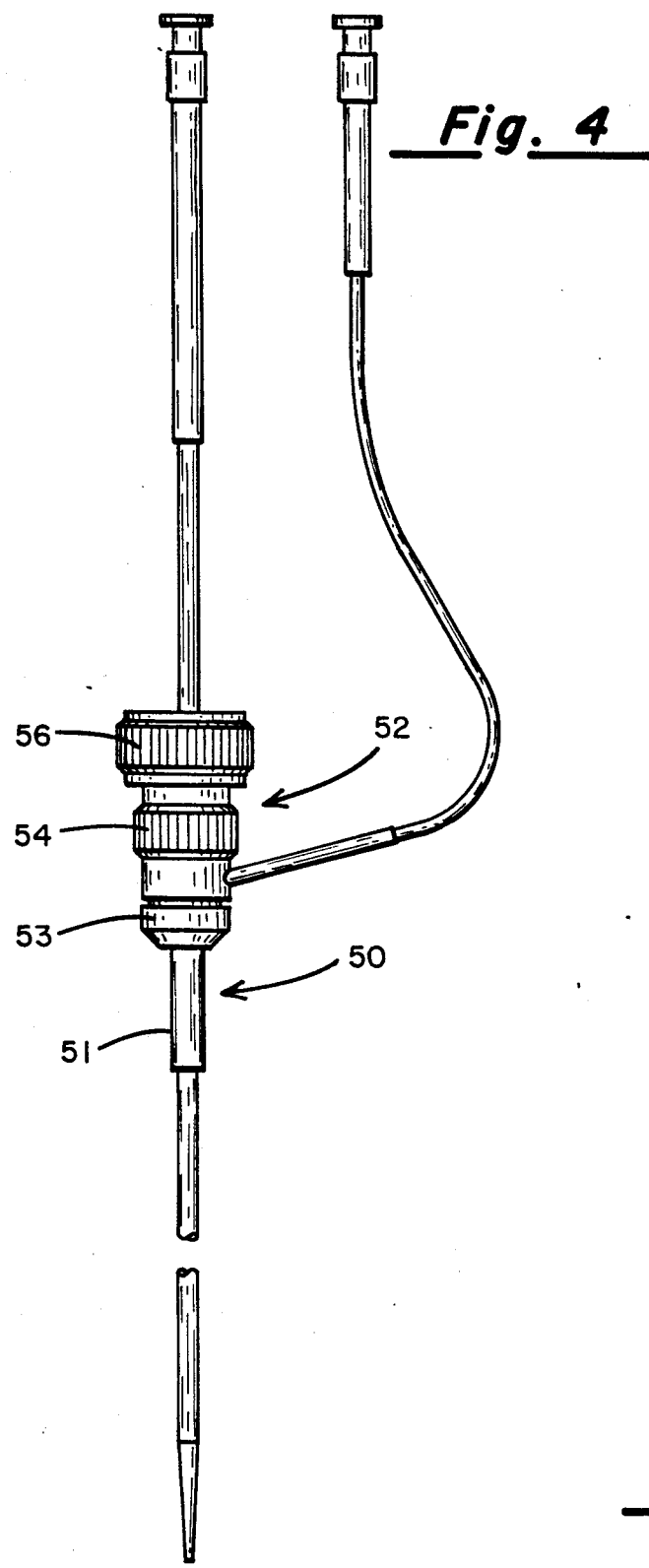
FIG. 4 is a plain view of an introducer of the type used in conjunction with the valve present invention.

As in shown in FIGS. 1 through 3, the preferred embodiment of the present invention is comprised of an integrally molded resilient valve body 10 which includes a distal cylindrical member 20, a central cylindrical member 30 and a proximal cylindrical member 40. These members are either integrally formed or secured together and aligned in face-to-face registration as best seen in the cross-sectional view of FIG. 2. All parts of the valve are preferably made of an elastomeric material such as natural rubber or silicone rubber. Members 20 and 40 have substantially the same outer diameter. However, the diameter of the intermediate member 30 is made larger to form an annular flange 31. Flange 31 is present to enable a tight seal to be made between the hemostasis valve 10 and the inner wall of the introducer housing (see FIGS. 5 and 6) into which the valve is placed.

With continued reference to FIG. 2, each of outer members 20 and 40 include an internal hollow chamber 21 and 41, respectively. Member 20 and member 40 each also includes a circular bore (22 and 42, respectively) passing through its thickest dimension such that the outside of the valve is in communication with its respective chamber. Circular bores 22 and 42 are coaxially aligned with respect to each other. The size of bore 42 depends upon the outside diameter of the catheter to be used in conjunction with the valve.

The presence of chambers 21 and 41 is important for proper functioning of the valve. These chambers make it possible for the valve to be held firmly in place by the introducer yet still permit the parts of the valve to stretch, move and be pliable as working catheters and guide wires are inserted or retracted. This is important to reduce drag on the catheter or guide wire and to enhance the physician's ability to manipulate the distal end of the catheter. Similarly, these chambers 21 and 41 reduce the amount of stress the valve would otherwise place on the catheter and permits the valve to go back to its original shape when the catheter is withdrawn.

Aligned with bores 22 and 42 and formed through the thickness dimension of the central member 30 is an angular slit 32. This slit is in communication on one side with chamber 21 on the other side with chamber 41. While slit 32 can be cut at any angle through the central section, this slit is preferably cut so that it is other than perpendicular with the proximal surface 33 and the distal surface 34 of the central member 30. For example, certain advantages are obtained if this slit is cut at an angle in the range from about 35° to 55° with 45° being preferred.

The modifications shown in FIGS. 1A through 3A were, in fact, made to aid cutting of the slit 32 at such a 45° angle with respect to the proximal and distal surfaces of the central member 30. As modified, the central member 30 is still cylindrical in shape. However, the shape of outer members 20 and 40 have been changed to include a central segment of reduced diameter (25 and 45, respectively) and an outer segment (26 and 46, respectively) of a diameter substantially equal to the diameter of central member 30. When so constructed, segments 26 and 46, in conjunction with central member 30, form a flange to allow a tight seal between the outer periphery of the valve body 10 and the inner wall of the introducer shown in FIGS. 5 and 6.

When the valve is constructed in accordance with the modified design of FIGS. 1A through 3A, formation of slit 32 at about a 45° angle is simplified. More particularly, an arcuate slit 28 can be made between a major portion of members 20 and 30. Likewise, a similar slit 48 is made between members 30 and 40. Once slits 28 and 48 are made, members 20 and 40 can be folded away to expose the location of member 30 where the slit 32 is to be made. Yet, when in use with an introducer, a tight seal is maintained between the introducer's inner wall and the outer perimeter valve body by pinching flanges 26 and 46 together against member 30 when the valve is secured within the inner valve receiving chamber of the introducer.

Figure 5:
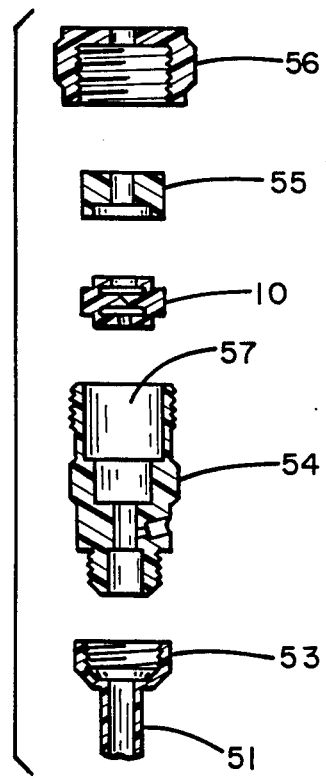
FIG. 5 is an exploded view of the portion of the introducer of FIG. 4 which holds the valve of the present invention.
Figure 6:
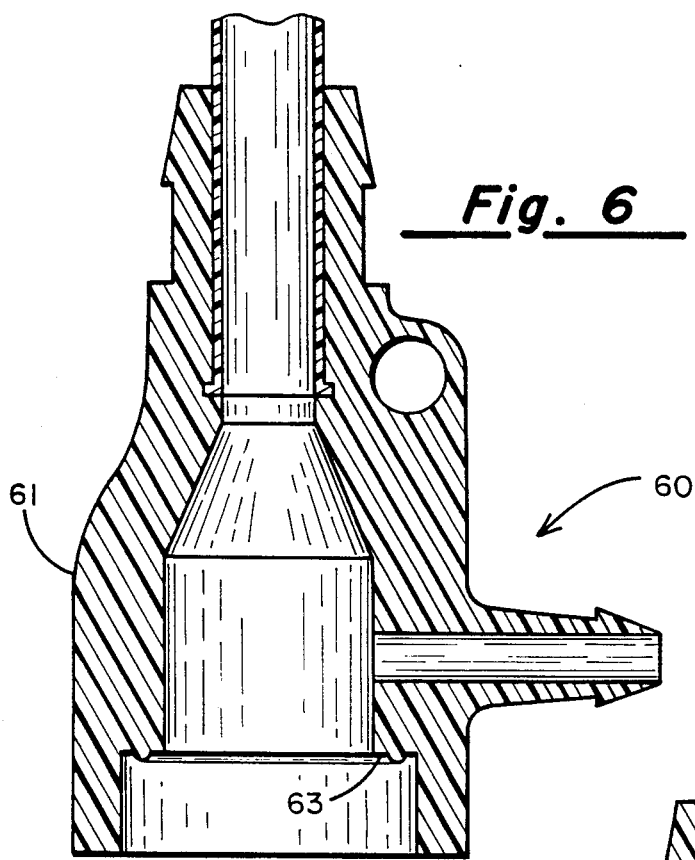
FIG. 6 is a plain view of an alternative style valve holder for an introducer.

As best shown in FIGS. 5 and 6, the introducer 50 includes an introduction tube 51 which is fixed to a receptacle assembly 52. The receptacle assembly 52 includes a union nut 53, a housing 54, a casing member 55, and a cover 56. The housing 54 includes inner chamber 57.

When the introducer 50 is assembled, the union nut 53 is mated to the housing 54. Reciprocal threads on the housing 54 and the nut 53 ensure a secure connection. Next, the valve member 10 is inserted into the inner chamber 57 of the housing 54. The casing member 55 is then placed in the inner chamber 57 over the valve member 10. Finally, the cover 56 is then secured to the housing 54. Again, reciprocal threading on the housing 54 and the cover 56 ensure a tight fit. When the introducer is so assembled, the valve 10 is securely held in place and a tight seal is formed between the flange 31 and the inner wall of the housing 54. Also, the cover 56, casing member 55 and housing 54 cooperate to pinch flanges 26 and 46 together against member 30. Finally, when so assembled, the introducer 50 includes a passage or lumen running its entire length which is selectively sealed by the valve member 10.

Figure 7:
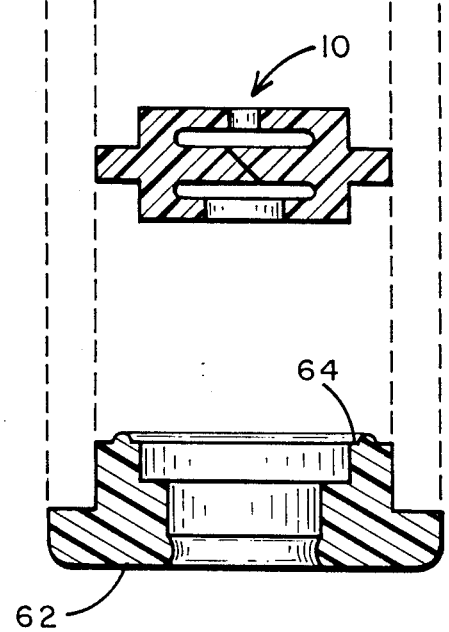
FIG. 7 is an exploded view of the valve holder of FIG. 6.
Figure 7:
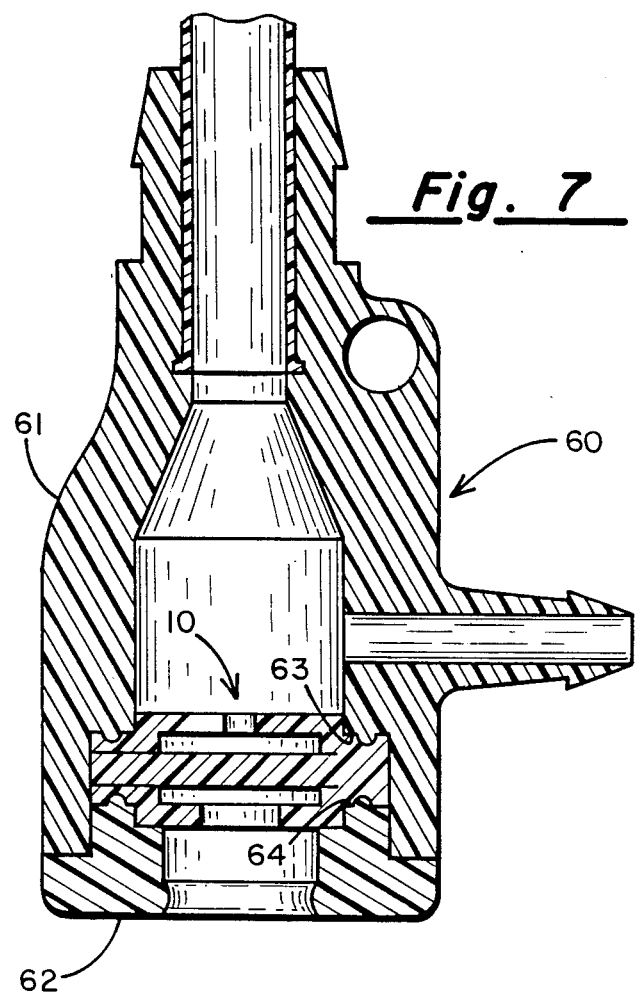

FIGS. 6 and 7 show an alternative style holder 60 for the valve 10. This holder 60 is comprised of a main housing 61 and a cover 62. Both housing 61 and cover 62 have a central lumen therethrough. The housing 61 is also characterized as including a shelf 63. Cover 62 has a similar shelf 64.

As best shown in FIG. 7, when assembled the valve 10 is seated within the housing 61 so that flange 26 of valve 10 is in contact with shelf 63. The cover 62 is then mated with the housing 61 so that the shelf 64 contacts flange 46 of the valve. The cover 62 and the housing 61 cooperate to pinch flanges 26 and 46 together about there periphery to hold the valve in place. While the compression fit between the outer wall of cover 62 and the inner wall of housing 61 may be sufficient in most instances to hold the parts in the desired assembled relation, for additional safety it is recommended that the cover 62 and housing 61 be ultrasonically welded so they become fused together.

After the introducer 50 is assembled with the valve 10 of the present invention in place, the introducer is then inserted into a vein or artery. Typically, then, a guide wire is advanced through the introducer until it reaches the valve. The physician will continue to advance the guide wire through the valve first through opening 42, then through slit 32 and finally through opening 22. When the guide wire has been passed through the valve, members 20, 30 and 40 cooperate to form a tight seal around the guide wire as it is advanced and manipulated within the circulatory system to the site of the blockage. Since the diameter of the guide wire is typically very small compared to the diameter of an angioplasty or angiographic catheter, member 30 is primarily responsible for providing the requisite tight seal around its outer diameter. Such a tight seal is made possible by the angled orientation of slit 32. Opening 22 also provides a seal around the guide wire.

Once the guide wire is properly positioned, a suitable catheter is advanced over the guide wire, into the introducer, through the valve 10 and into the vascular system. Again, the valve parts, and particularly the elastomeric material on either side of slit 32 will close down around the catheter to form a tight seal.

Important advantages of the present invention over the prior art become apparent when the penetrating guide wire and catheter are removed. The fact that the flaps formed in the central member 30 by slit 32 do not merely abut each other, but rather overlap to provide a larger sealing surface and pressure on either side tends to compress the angled slit to ensure a quick, tight, self-adjusting lip seal. This is accomplished with the present invention with minimal resistance to the insertion, manipulation and removal of the catheter through the valve.

For exemplary purposes, and not by way of limitation, the article of the present invention may have an O.D. of about 0.30 inches, an overall width of 0.115 inches, a proximal and distal cylindrical member whose diameters are 0.218 inches, one such cylindrical member having a 0.032 inch bore therethrough and the other having a bore of a diameter in the range from 0.042 inches to 0.060 inches to accommodate working catheters of differing sizes. The hollow chambers may be 0.020 inches deep and have a diameter of 0.168 inches.

The above-description of the present invention should, in all respects, be deemed illustrative rather than limiting. This is particularly true since the invention may be embodied in other specific forms without deviating from its spirit or essential characteristics. Therefore, all changes which come within the meaning and range of equivalency of the claims set forth below are intended to be embraced therein.

What is claimed is:

1. An article of manufacture comprising an integrally molded resilient hemostasis valve body having a central passage extending therethrough from its proximal to its distal side for receiving an elongated implement, said article including:
    (a) a proximal cylindrical member having a bore therethrough of a first diameter;
    (b) a distal cylindrical member having a bore of a second diameter therethrough;
    (c) a central cylindrical disk member having a proximal base in face-to-face registration with said proximal cylindrical member, a distal base in face-to-face registration with said distal cylindrical member, and a straight slit extending therethrough;
    (d) a proximal chamber between a portion of the proximal base of said central cylindrical member and said proximal cylindrical member; and
    (e) a distal chamber between a portion of the distal base of said central cylindrical member and said distal cylindrical member.

2. The article as in claim 1 wherein said proximal cylindrical member and said distal cylindrical member each having a first predetermined diameter.

3. The article of claim 2 wherein said central cylindrical member has a second predetermined diameter which is greater than said first predetermined diameter.

4. The article of claim 1 wherein said valve body is made of an elastomeric material.

5. The article of claim 4 wherein said elastomeric material is silicone rubber.

6. The article of claim 4 wherein said elastomeric material is natural rubber.

7. The article of claim 1 wherein said continuous slit extending through said central cylindrical member is at an angle other than 90 degrees to its proximal base and its distal base.

8. The article of claim 7 wherein said angle is in the range of from about 35° to 55° with respect to said proximal base and said distal base of said central cylindrical member.

9. An article of manufacture comprising an integrally molded resilient valve body including:
    (a) a proximal gasket member having an inner segment with a central bore therethrough and an outer segment having a central bore therethrough which is larger than the bore through the inner segment;
    (b) a distal gasket member having an inner segment with a central bore therethrough and an outer segment with a central bore therethrough which is larger than the bore through the inner segment; and
    (c) a central gasket member having an outside diameter equal to the outside diameter of the outer segments of said proximal and distal gasket members, said central gasket member including a proximal base in face-to-face registration with the inner segment of the proximal gasket member and a distal base in face-to-face registration with the inner segment of the distal gasket member, said central gasket member also including a slit therethrough which is at a predetermined angle other than 90° with respect to said proximal base and said distal base.

10. The apparatus of claim 7 wherein the outer segments of said proximal and distal gasket members each have an outside diameter which is less than the outside diameter of the inner segments of said gasket members.

11. The apparatus of claim 7 wherein said predetermined angle is in the range from about 35° to about 55° with respect to the proximal and distal bases of said gasket members.

* * * * *